United States Patent
He et al.

(10) Patent No.: US 6,871,090 B1
(45) Date of Patent: Mar. 22, 2005

(54) SWITCHING REGULATOR FOR IMPLANTABLE SPINAL CORD STIMULATION

(75) Inventors: Yuping He, Santa Clarita, CA (US); David K. L. Peterson, Saugus, CA (US)

(73) Assignee: Advanced Bionics Corporation, Valencia, CA (US)

( * ) Notice: Subject to any disclaimer, the term of this patent is extended or adjusted under 35 U.S.C. 154(b) by 490 days.

(21) Appl. No.: 09/975,430

(22) Filed: Oct. 10, 2001

Related U.S. Application Data

(60) Provisional application No. 60/240,147, filed on Oct. 13, 2000.

(51) Int. Cl.[7] ................................. A61N 1/08
(52) U.S. Cl. ............... 607/2; 607/57; 607/48; 607/63
(58) Field of Search ................ 607/55–57, 60, 607/65, 66, 117, 34, 4, 5, 7, 32, 2, 48, 63, 43; 363/15, 20; 320/33, 40

(56) References Cited

U.S. PATENT DOCUMENTS

| | | | | |
|---|---|---|---|---|
| 3,738,371 A | * | 6/1973 | Raddi et al. ................. 607/29 |
| 3,867,949 A | * | 2/1975 | Schwalm et al. ............. 607/12 |
| 5,265,588 A | | 11/1993 | Nelson et al. ................. 607/5 |
| 5,363,286 A | * | 11/1994 | Tsuchiya ....................... 363/8 |
| 5,372,605 A | * | 12/1994 | Adams et al. ................. 607/5 |
| 5,522,865 A | | 6/1996 | Schulman et al. ............ 607/56 |
| 5,674,248 A | * | 10/1997 | Kroll et al. .................... 607/5 |
| 5,745,350 A | | 4/1998 | Archer et al. ................ 363/15 |
| 6,094,597 A | | 7/2000 | Wold ............................ 607/5 |
| 6,115,272 A | * | 9/2000 | Pasternak ................... 363/60 |
| 6,125,300 A | | 9/2000 | Weijand et al. .............. 607/66 |
| 6,172,480 B1 | * | 1/2001 | Vandelac ................... 320/125 |
| 6,185,460 B1 | * | 2/2001 | Thompson .................. 607/16 |
| 6,223,080 B1 | * | 4/2001 | Thompson .................. 607/16 |
| 6,304,467 B1 | * | 10/2001 | Nebrigic .................... 363/49 |

* cited by examiner

*Primary Examiner*—Jeffrey R. Jastrzab
(74) *Attorney, Agent, or Firm*—Kenneth L. Green; Bryant R. Gold

(57) ABSTRACT

An improved switching regulator for implantable medical devices includes a control circuit with a capacitor divider to conserve energy, and selectable duty cycles to efficiently match the duty cycle to the charge level in a holding capacitor. The switching regulator charges the holding capacitor to commanded voltage levels, and the holding capacitor provides current for tissue stimulation. The commanded voltage level is reached by "pumping-up" the holding capacitor with the output of the switching regulator. For control purposes, the high voltage (i.e., the voltage across the holding capacitor) is divided between a fixed capacitor and a variable capacitor, and the voltage between the fixed capacitor and the variable capacitor (i.e., the divided voltage) is compared to a reference voltage. The result of the comparison is used to turn-off the switching regulator once the commanded voltage level is reached. The switching duty cycle is set to one of two values. At start-up, or when the output voltage drops below a determined threshold, a low duty cycle is used. Once the output voltage reaches the threshold, a higher duty cycle is used.

20 Claims, 4 Drawing Sheets

SWITCHING REGULATOR FOR IMPLANTABLE SPINAL CORD STIMULATION

The present application claims the benefit of U.S. Provisional Application Ser. No. 60/240,147, filed Oct. 13, 2000, which application is incorporated herein by reference.

BACKGROUND OF THE INVENTION

The present invention relates to implantable medical devices, and more particularly to a voltage converter, for use within an implantable Spinal Cord Stimulation (SCS) system, or similar implantable device, that uses a switching regulator to provide a voltage step-up function.

Many implantable medical devices, such as neural stimulators, sensors, and the like, utilize a battery as a primary source of operating power. Other types of implantable devices, such as known cochlear stimulators, rely on transcutaneous inductive power transmission from an external device to the implantable device, where an induced voltage is thereafter rectified and filtered in order to provide the primary operating power for the implantable device. In both types of devices, a battery-powered device or an RF-powered device, there: is a frequent need to derive other operating voltages within the device from the primary power source. That is, there is a frequent need to step up the voltage of the primary power source to a higher voltage in order to, e.g., generate a high stimulation current.

In order to perform the voltage step-up or step-down function, it is known in the art to use a charge-pump voltage converter circuit. Charge pump circuits typically rely on a network of capacitors and switches in order to step up and step down a primary power source. For example, in order to step up a primary voltage source, a network of capacitors, e.g., four capacitors, may be connected in parallel through a switching network, and kept in the parallel connection until each capacitor is charged to the voltage level of the primary power source. In systems where a battery is used as the primary power source, the battery voltage is the voltage of the primary power source. Once thus charged, the capacitors are switched so that they are connected in series, thereby effectively creating a voltage across the series connection that is an integer multiple of (in this example, four times) the voltage of the primary power source. The charge associated with this higher voltage may then be transferred to another capacitor, e.g., a holding capacitor, and this process (of charging parallel-connected capacitors, switching them in series, and then transferring the charge from the series connection to a holding capacitor) is repeated as many times as is necessary in order to pump up the charge on the holding capacitor to a target voltage that is higher than the voltage of the primary power source.

While charge-pump circuits have proven effective for performing step up and step down functions, such circuits require a large number of capacitors to provide fine resolution of voltage. Charge pump circuits with course voltage resolution (i.e., a small number of capacitors) result in inefficient power use because the current resulting from the excess voltage is dissipated. Charge pump circuits with fine resolution require large numbers of capacitors, and are therefore not well suited for small implantable medical devices. Moreover, charge pump circuits tend to be relatively slow (i.e., are limited in peak current) and inefficient in operation.

Switching regulators have been used to overcome some of the limitations of charge-pump circuits. Known switching regulators utilize a closed loop voltage control. Such closed loop voltage control includes a resistor divider to sample either the voltage output of the switching regulator, or the voltage of an energy storage device being charged by the switching regulator, e.g., a holding capacitor. The voltage of the node between the resistors is compared to a reference voltage and the difference between the reference voltage and the node voltage is used by control logic to turn the switching regulator on or off, and thereby control the output voltage. Unfortunately, the use of resistors in such a circuit consumes energy continuously. Further, known switching regulators use a single duty cycle, and the duty cycle of a switching regulator that is best for low voltages may not be the best duty cycle for high voltages.

What is needed, therefore, is a voltage converter circuit that is able to perform the step up function, efficiently, quickly, and without having to rely on the use of a large number of capacitors, and which operates more efficiently than known switching regulators.

SUMMARY OF THE INVENTION

The present invention addresses the above and other needs by providing a switching regulator, for use within implantable devices such as a Spinal Cord Stimulation (SCS) system, including a control circuit with a capacitor divider, and selectable duty cycles to efficiently match the duty cycle to the charge level in a holding capacitor. The switching regulator charges a holding capacitor to commanded voltage levels, and the holding capacitor provides current for tissue stimulation. Commanded voltages, generally higher than the source voltage level (typically a battery voltage), are achieved by "pumping-up" the holding capacitor with the output of the switching regulator. The holding capacitor is connected, through a diode, to the output of a step-up switching regulator inductor (hereafter "switching inductor") which is the heart of the switching regulator. Each time the power to the switching inductor is cycled on and off, the inertia of the current flowing through the switching inductor forces current to flow into the holding capacitor and pushes the charge (and therefore voltage level) in the holding capacitor higher. The diode prevents a reverse current flow out of the holding capacitor.

For control purposes, the voltage across the holding capacitor (referred to hereafter as "high voltage") is sampled by a capacitor divider. The high voltage is divided between a fixed capacitor and a variable capacitor, and the voltage between the fixed capacitor and the variable capacitor (i.e., the "divided voltage") is compared to a reference voltage. The commanded voltage of the holding capacitor is achieved by adjusting the variable capacitor. The result of the comparison is used to turn off the switching regulator once the commanded output voltage level is reached.

In accordance with one aspect of the invention, there is provided a control circuit with a capacitor divider comprising a fixed capacitor and a variable capacitor. The capacitor divider performs the same function that a resistor divider performs in known systems, but without the energy consumption of the resistors. The capacitance of the variable capacitor is adjusted so that when the voltage across the holding capacitor reaches the commanded level for generation of a stimulation pulse, the voltage level between the fixed and variable capacitors (i.e., the divided voltage) will be equal to a fixed reference voltage.

It is a feature of the present invention to provide an on/off control to the switching regulator based on the result of comparing the divided voltage level of the capacitor divider to a reference voltage. Once the divided voltage exceeds the reference voltage, the switching regulator is turned off.

In accordance with another aspect of the invention, the switching regulator may operate in one of two duty cycles. When the switching regulator is turned on, or if the voltage of the holding capacitor drops below a threshold, a low duty cycle is selected. When the voltage of the holding capacitor exceeds the threshold, a higher duty cycle is selected. By matching the duty cycle to the voltage of the holding capacitor, saturation of the inductor core is avoided, thus providing efficient operation of the switching regulator.

It is a further feature of the invention to periodically zero the fixed and the variable capacitors. By periodically discharging the fixed and the variable capacitors to ground, an accumulation of biases that might degrade performance is prevented.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
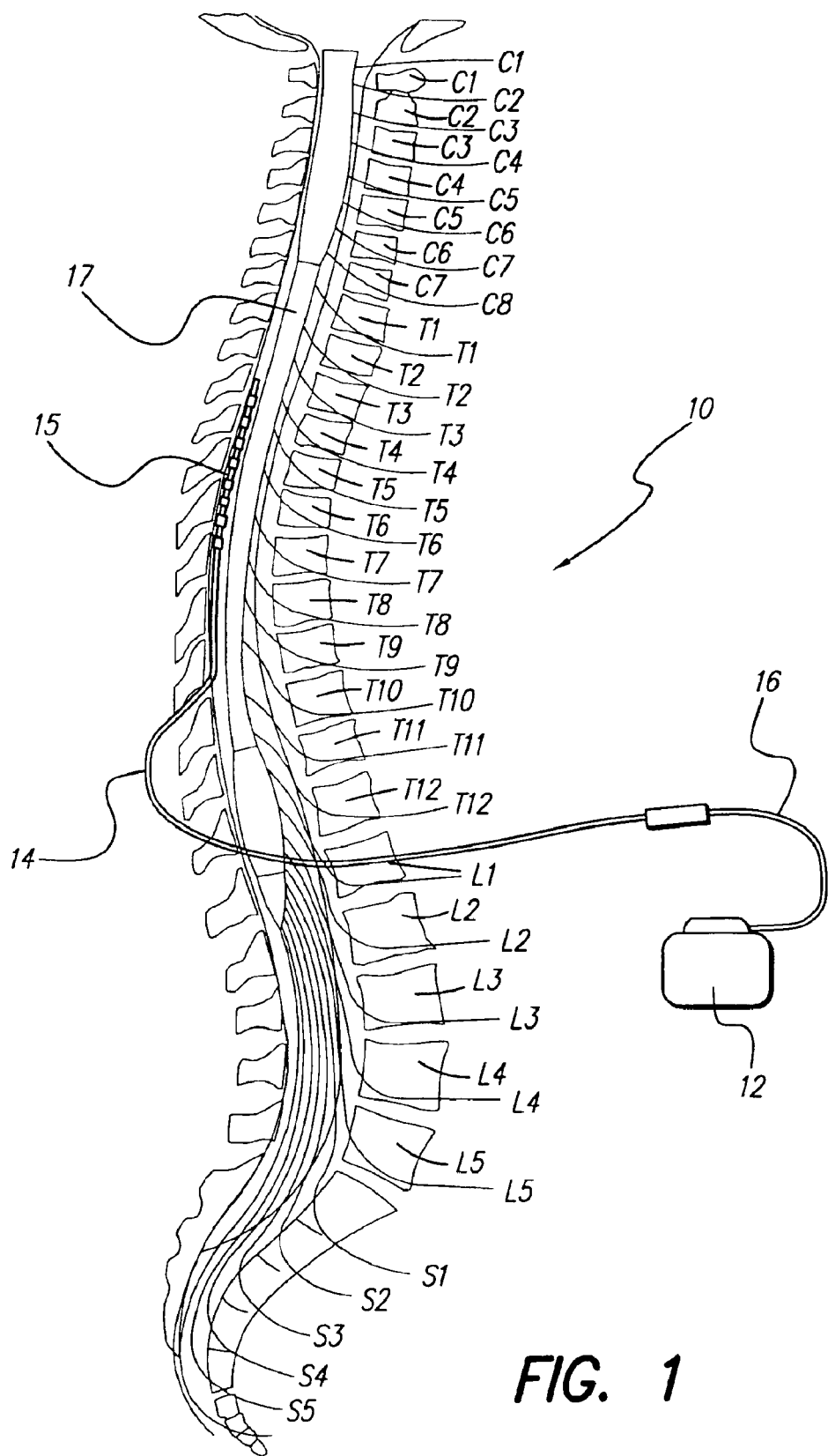
FIG. 1 depicts a typical implantation of a Spinal Cord Stimulation (SCS) system in a patient.

The improved switching regulator of the present invention efficiently provides an implantable device with a multiplicty of voltage levels for tissue stimulation or other uses. A representative implantable Spinal Cord Stimulation (SCS) system 10 that would benefit from the present invention is shown in FIG. 1. The SCS system 10 comprises an Implantable Pulse Generator (IPG) 12 electrically connected by an electrode lead extension 16 to a proximal end of an electrode lead 14. An electrode array 15, residing on a distal end of the electrode lead 14, is implanted along spinal cord 17 of a patient. The IPG 12 provides stimulation current that is conducted by the electrode lead extension 16 and electrode lead 14 to the electrode array 15. The electrode array 15 provides the stimulation current to the spinal cord 17 to mask sensations of pain felt by the patient, or for other purposes. Such an SCS system 10 is one of many applications of the present invention. Any application requiring efficient voltage conversion could benefit from the invention, and is within the scope of the present invention.

Figure 2:
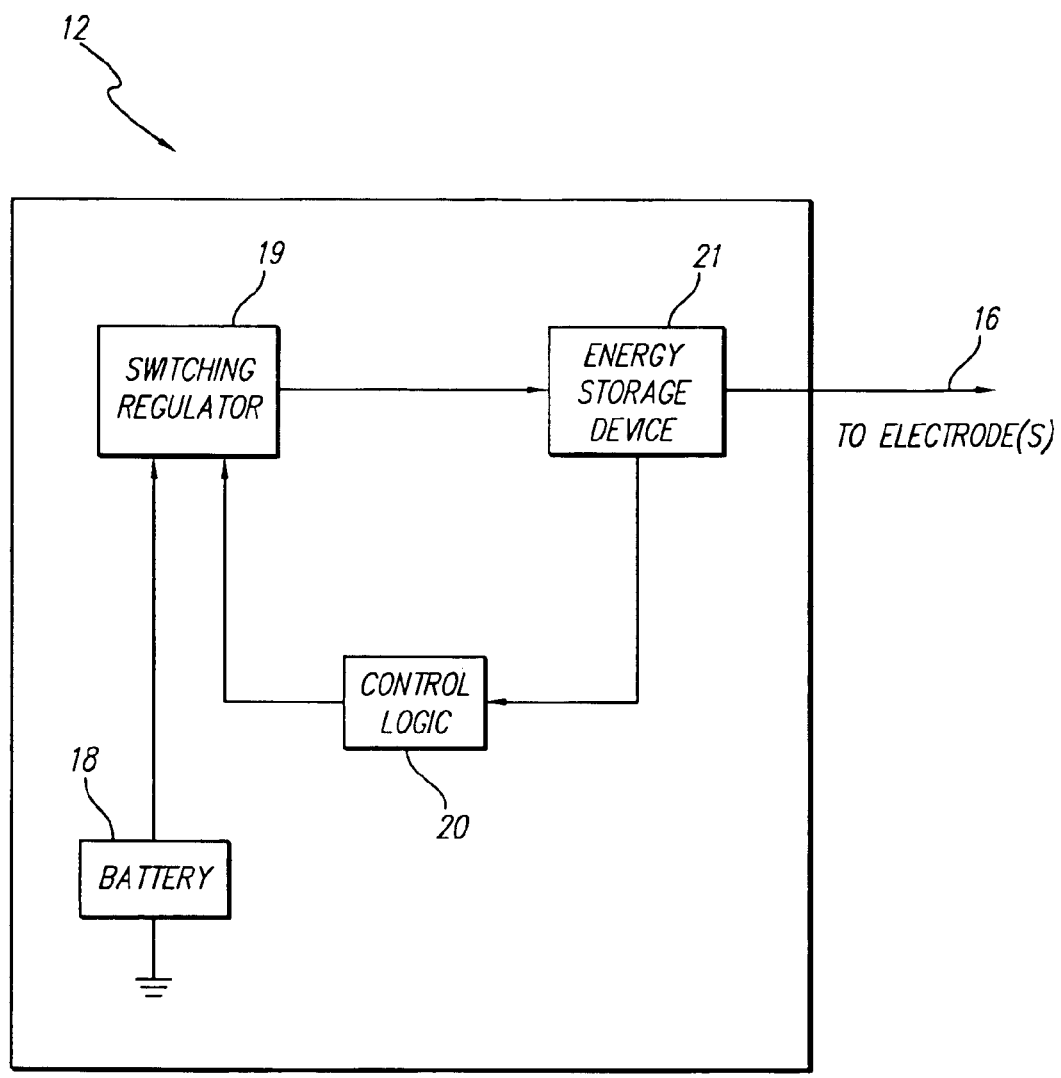
FIG. 2 shows a high level functional block diagram of a switching regulator and control system.

A high level functional block diagram of a switching regulator utilizing the present invention is shown in FIG. 2 residing with the IPG 12. A battery 18 provides primary power to a switching regulator 19. The switching regulator 19 generates current: that charges an energy storage device 21. Control logic 20 monitors a voltage level associated with the energy storage device 21, and when the voltage level reaches a commanded or predetermined voltage, the control logic 20 turns off the switching regulator 19. The control logic 20 also controls a duty cycle for the switching regulator.

Figure 3:
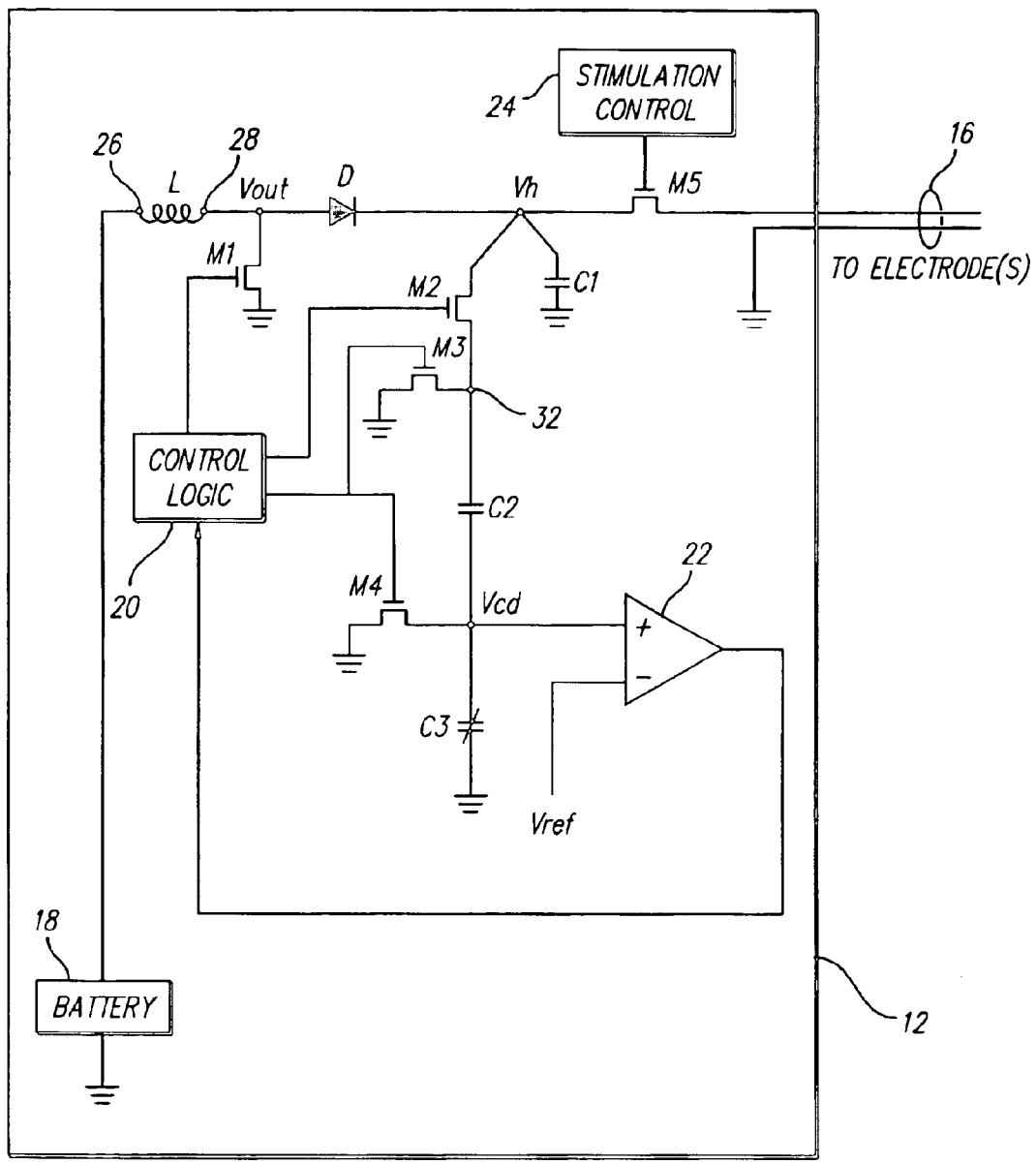
FIG. 3 shows a circuit diagram of a preferred embodiment of the switching regulator and control circuit of the present invention.

A detailed circuit diagram for a preferred embodiment of the present invention is shown in FIG. 3. The battery 18 provides primary operating power (voltage and current) to an inductor input node 26 of a step-up switching regulator inductor (hereafter the "switching inductor") L. An inductor output node 28 is connected to a node Vout. A first switch M1 is connected between the node Vout and ground, and the switch M1 is controlled by a first control signal from the control logic 20. The cathode side of a diode D is also connected to the node Vout, and the anode side of the diode D is connected to a node. Vh. A holding capacitor C1 is connected between the node Vh and ground. The control logic 20 controls the switch M1 using a very high frequency (preferably 500 KHz or more) close/open signal. When the switch M1 is closed, current flows from the battery 18 through the switching inductor L and through the switch M1 to ground. A magnetic field develops in the switching inductor L due to the current flowing through the switching inductor L. When the control logic 20 opens the switch M1, the magnetic field around the switching inductor L resists a change in the current flow, and briefly forces the current flow to continue. The only path for the current flow is through the diode D and into the holding capacitor C1. During this time (when the switch M1 is open, but current is still flowing through the switching inductor L) the voltage at the node Vout and at the node Vh may rise above the battery voltage to the level required for the current to flow into the holding capacitor C1. On each cycle of the first switch M1, the voltage across the holding capacitor C1 rises, thereby providing a voltage step-up. Thus, by controlling the switch M1, the control logic 20 may control both, the frequency and the duty cycle of the switching regulator, thereby providing a modulated current surge through the diode D to the holding capacitor C1, wherein the charge in the holding capacitor C1 is increased each time the first switch M1 is opened.

Continuing with FIG. 3, a second switch M2 controlled by a second control signal, a node 32 residing on a first lead, fixed capacitor C2, a node Vcd, and a variable capacitor C3 are electrically connected in series between the node Vh and ground. The combination of the fixed capacitor C2 and the variable capacitor C3 comprises a capacitor divider. A third switch M3 controlled by a third control signal is connected between ground and the node 32. A fourth switch M4 controlled by a fourth control signal is connected between the node Vcd and ground. The switch M2, the switch M3, and the switch M4, are all controlled by control logic 20.

The capacitor divider develops a divided voltage at the node Vcd. The node Vcd is connected to a first input of a comparator 22, and a fixed reference voltage Vref is connected to a second input of the comparator 22. The capacitance of the variable capacitor C3 is set so that the divided voltage at node Vcd will be equal to the reference voltage Vref when the voltage at the node Vh is the voltage required to provide the desired stimulation current.

The comparator 22 processes the first input from the node Vcd and the second input from the reference voltage Vref, and generates an error signal representative of the difference between the reference voltage Vref and the, divided voltage at the node Vcd (which divided voltage varies proportionally with the voltage at the node Vh). The error signal is sent to the control logic 20. When the control logic 20 receives an error signal from the comparator 22 indicating that the divided voltage is greater than the reference voltage Vref, the control logic 20 switched to an OFF mode, thus turning the switching regulator off.

Those skilled in the art will recognize that some of the control functions may be reallocated between circuit elements. For example, the comparator 22 may output an on/off signal to the control logic 20 instead of an error signal. The mere reallocation of such functions is intended to come within the scope of the present invention.

The switch M3 and the switch M4 are provided to short the fixed capacitor C2 and the variable capacitor C3 to ground to periodically discharge the capacitor C2 and the capacitor C3 (preferably at a 100 msec rate) to prevent the build up of bias voltages. Switch M2 disconnects the node Vh from the fixed capacitor C2 when the switch M3 or the switch M4 are closed, so that the holding capacitor C1 is not discharged.

Thus, with reference to FIG. 3, it is seen that the control logic 20 monitors the voltage at node Vh (by monitoring the voltage at node Vcd, as described above) to control the charge level of the holding capacitor C1. The control logic 20 also may control the duty cycle of the switching regulator L by controlling the percentage of the period that the switch M1 is closed. The duty cycle may be selected from two or more selectable duty cycles. When the switching regulator is turned on, or when the voltage at the node Vh (preferably measured by comparing the divided voltage at node Vcd to a low duty cycle threshold) drops below a threshold (preferably twice the battery voltage) a low selectable duty cycle (preferably 20% or lower) is selected. Otherwise, a high selectable duty cycle (preferably 50% or higher) is selected. Preferably, the duty cycle is adjusted by varying the period of the switching regulator (thereby varying the frequency of the switching regulator), wherein the length of time that the, switch M1 is open is varied, but the length of time that the switch M1 is closed is not changed. Those skilled in the art will recognize that several duty cycles, or a continuously variable duty cycle may be adapted in place of two selectable duty cycles described herein, and are intended to come within the scope of the present invention.

A switch M5 shown in FIG. 3 is connected between the node Vh and the electrode lead extension 16, The switch M5 is controlled by stimulation control circuitry 24. When the switch M5 is closed, the holding capacitor C1 discharges through the electrode array 15 of FIG. 1, and provides electrical stimulation to the spinal cord 17.

Those skilled in the art will recognize that many variations of the circuit shown in FIG. 3 are available for the control of a switching regulator. The heart of the present invention is the use of a capacitor divider and/or multiple duty cycles to efficiently step-up voltage. Other embodiments of a switching regulator circuit, which also use a capacitor divider or multiple duty cycles, are therefore within the scope of the present invention.

Figure 4:
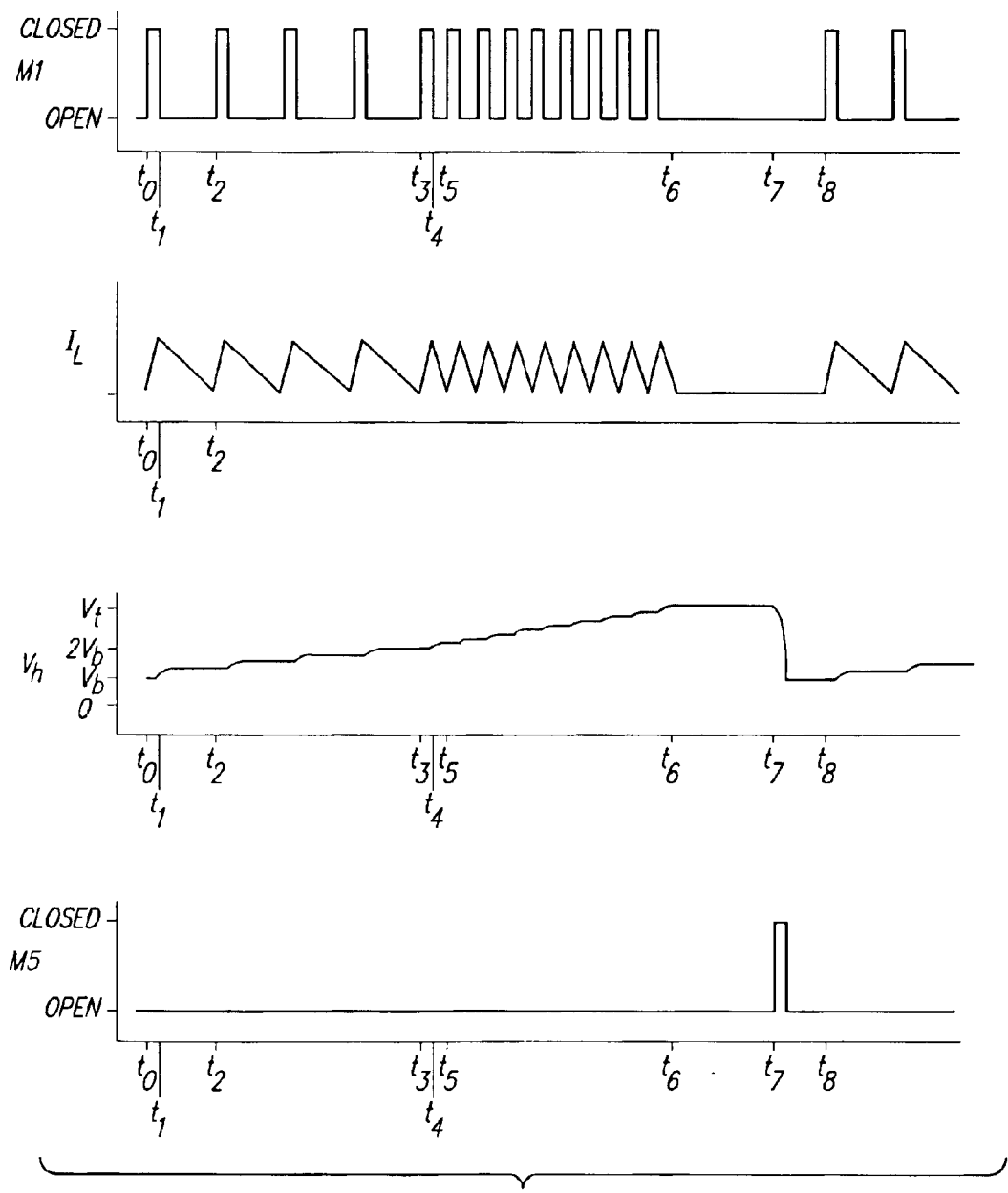
FIG. 4 shows parallel plots of a first switch M1, the current flowing through a switched inductor L, the voltage level in a holding capacitor Vh, and a fifth switch M5.

Parallel plots of the position of the first switch M1, the current $I_L$ flowing through the switching inductor L, the voltage level at the node Vh, and the position of the fifth switch M5, are provided in FIG. 4. The switching regulator is turned on at $t_0$. The switch M1 is switched from open to closed at $t_0$, and remains closed for twenty percent of the period of the switching regulator (i.e., a twenty percent duty cycle). When the switch M1 closes at $t_0$, current $I_L$ begins to flow through the switching inductor L. At $t_1$, the switch M1 is opened, and the current $I_L$ begins to drop. The inductor L resists an immediate drop in current flow, and as a result some current flows through the diode D and into the holding capacitor C1 (FIG. 3), increasing the charge on the capacitor C1 and the voltage at the node Vh. At $t_2$ the cycle begins again with the switch M1 closing.

The switching regulator continues to operate at a twenty percent duty cycle (a low duty cycle) until $t_3$ when the voltage at the node Vh is at least twice the battery voltage Vb. At $t_3$, the switch M1 closes, and remains closed for the same length of time as the switch M1 was previously closed. At $t_4$ the switch M1 opens and current flows into the capacitor C1, further increasing the voltage at the node Vh. However, after $t_3$, the total period of the switching regulator is reduced (with an associated increase in frequency) so that the length of time the switch M1 is open (the time from $t_4$ to $t_5$) is now the same as the length of time the switch M1 is closed (the time from $t_3$ to $t_4$) resulting in a fifty percent duty cycle. At $t_5$ another fifty percent duty cycle (a high duty cycle), begins. The high duty cycles continue until the voltage at the node Vh reaches the target voltage Vt. At $t_6$, the voltage at the node Vh reaches Vt, and the switching regulator is turned off. At $t_7$ the fifth switch M5 closes, and the holding capacitor C1 is discharged through the electrode lead extension 16 to the electrode array 15 (FIG. 1). At $t_8$ the process of charging the holding capacitor C1 is again initiated and carried out as described above.

While the invention herein disclosed has been described by means of specific embodiments and applications thereof, numerous modifications and variations could be made thereto by those skilled in the art without departing from the scope of the invention set forth in the claims.

What is claimed is:

1. An improved switching regulator for an implantable device, wherein the switching regulator includes control circuitry, and wherein the control circuitry provides at least one control parameter for the switching regulator, the improvement comprising:
   a capacitor divider comprising at least two capacitors, and
   a divided voltage, wherein the divided voltage is the voltage between two of the at least two capacitors;
   wherein the control circuitry provides at least one control parameter for the switching regulator based on the divided voltage.

2. The improved switching regulator of claim 1 wherein at least one of the at least two capacitors is a variable capacitor.

3. The improved switching regulator of claim 2 wherein:
   the switching regulator charges an energy storage device connected to a circuit node Vh;
   the capacitor divider is connected between the node Vh and ground;
   the control circuitry includes a reference voltage; and
   the variable capacitor is set to a capacitance so that the divided voltage equals the reference voltage when a desired voltage is present at the node Vh.

4. The improved switching regulator of claim 3 wherein the switching regulator includes an on command and an off command, wherein the switching regulator has a current output while the control circuitry is providing an on command, and wherein the switching regulator has no output while the control circuitry is providing an off command, and wherein the control circuitry provides an on command when the divided voltage is less than the reference voltage, and wherein the control circuitry provides an off command when the divided voltage is at least equal to the reference voltage.

5. The improved switching regulator of claim 4 wherein the switching regulator includes a comparator, and wherein the comparator compares the divided voltage to a reference voltage.

6. The improved switching regulator of claim 1 wherein the switching regulator includes a duty cycle, and wherein the improvement further includes providing at least two selectable duty cycles for the switching regulator, wherein one of the at least two selectable duty cycles is selected for use as the duty cycle based on a comparison of the divided voltage to a low duty cycle threshold.

7. The improved switching regulator of claim 6 wherein the low duty cycle threshold corresponds to twice the voltage of a battery providing voltage and current to the switching regulator.

8. The improved switching regulator of claim 1 wherein the at least two capacitors comprises at least two capacitors connected in series.

9. The improved switching regulator of claim 1 wherein the control circuitry comprises the capacitor divider, a comparator, and control logic.

10. An improved power supply for an implantable device, the power supply comprising:
   a battery;
   control circuitry;
   a step-up switching regulator inductor with an input connected to the battery and an output connected to a node Vout;
   a first switch connected between the node Vout and ground, wherein the first switch is controlled by the control circuitry;
   a diode including a cathode side and an anode side, wherein the cathode side is connected to the node Vout, and the anode side is connected to a node Vh;
   a holding capacitor connected between the node Vh and ground;
   a second switch controlled by the control circuitry;
   a first lead;
   a fixed capacitor;
   a node Vcd; and
   a variable capacitor;
   wherein the second switch, the first lead, the fixed capacitor, the node Vcd, and the variable capacitor are electrically connected in series between Vh and ground;
   a third switch connected between the first lead and ground, wherein the third switch is controlled by the control circuitry;
   a fourth switch connected between the node Vcd and ground, wherein the fourth switch is controlled by the control circuitry; and
   a comparator having a first input connected to the node Vcd, a second input connected to a reference voltage Vref, and a comparator output provided to the control circuitry.

11. The improved power supply of claim 10 further including a fifth switch connected between the node Vh and an electrode lead extension, wherein the fifth switch is controlled by stimulation control.

12. The improved power supply of claim 10 wherein the control circuitry provides control signals comprising:
   a first control signal to the first switch adapted to control a frequency and a duty cycle of current flow through the step-up switching regulator inductor, thereby providing a modulated current surge through the diode to the holding capacitor, wherein the charge in the holding capacitor is increased each time the first switch is opened;
   a second control signal to the second switch adapted to connect or disconnect the fixed capacitor and the variable capacitor from the node Vh, whereby the fixed capacitor and the variable capacitor may be shorted to ground without shorting the node Vh to ground; and
   a third control signal to the third switch and a fourth control signal to the fourth switch, whereby the fixed capacitor and the variable capacitor may be shorted to ground to discharge the fixed capacitor and the variable capacitor.

13. The improved power supply of claim 12, wherein the duty cycle is selectable from at least two selectable duty cycles.

14. The improved power supply of claim 13, wherein the duty cycle selected from the at least two selectable duty cycles is selected to provide efficient operation of the power supply.

15. An improved switching regulator for an implantable device, wherein the switching regulator includes a duty cycle, the improvement comprising:
   a capacitor divider;
   a divided voltage between at least two capacitors of the capacitor divider; and
   two or more selectable duty cycles wherein the duty cycle is selectable from the two or more selectable duty cycles based on the divided voltage.

16. The improved switching regulator of claim 15 wherein the duty cycle is selectable from the at least two selectable duty cycles is based on the one of the at least two selectable duty cycles which provides efficient operation of the power supply.

17. The improved switching regulator of claim 16 wherein the at least two selectable duty cycles comprise a first selectable duty cycle that is twenty percent or lower, and a second selectable duty cycle that is fifty percent or higher.

18. A method to efficiently operate a switching regulator, comprising:
   providing a voltage input to a switching inductor;
   providing a switched path from the switching inductor to ground;
   providing a second path from the switching inductor to a storage device;
   measuring the voltage level of the storage device using a capacitor divider; and
   controlling the switching regulator based on the voltage level.

19. The method of claim 18 wherein measuring the voltage level of the storage device using a capacitor divider comprises comparing a divided voltage between two of at least two capacitors to a reference voltage, and wherein controlling the switching regulator further comprises turning the switching regulator off when the divided voltage is at least the reference voltage.

20. The method of claim 18 wherein measuring the voltage level of the storage device using a capacitor divider comprises measuring a divided voltage between two of at least two capacitors to a reference voltage, and wherein controlling the switching regulator further comprises selecting a duty cycle for the switched inductor based on the divided voltage.

* * * * *